US00PP18242P2

(12) United States Plant Patent
Sanders

(10) Patent No.: US PP18,242 P2
(45) Date of Patent: Nov. 20, 2007

(54) **NEW GUINEA *IMPATIENS* PLANT NAMED 'INGMULROS'**

(50) Latin Name: *Impatiens hawkeri*
Varietal Denomination: Ingmulros

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/436,744

(22) Filed: May 18, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

PP11,412 P * 6/2000 Kientzler ..... Plt./318

OTHER PUBLICATIONS

UPOV ROM GTITM Computer Database, GTI Jouve Retrieval Software 2006/04 Citations for Ingmulros.*

* cited by examiner

*Primary Examiner*—Wendy C. Haas
(74) *Attorney, Agent, or Firm*—Bruce Vrana

(57) ABSTRACT

A new and distinct cultivar of New Guinea *Impatiens* plant named 'Ingmulros' characterized by its small light red colored flowers with a dark spot in the center, very early flowering and very floriferous, with small foliage, good heat tolerance, nice spreading growth habit with excellent basal branching and good vigor.

1 Drawing Sheet

Latin name of the genus and species of the plant claimed: *Impatiens hawkeri.*
Varietal denomination: 'Ingmulros'.

BACKGROUND OF THE NEW PLANT

The present invention comprises a new and distinct New Guinea *Impatiens* plant botanically known as *Impatiens hawkeri* and referred to by the cultivar name 'Ingmulros.'

The new cultivar was developed in a controlled breeding program conducted by the inventor in Enkhuizen, Netherlands. The new New Guinea *Impatiens* cultivar is very floriferous with small flowers and small foliage, early flowering on compact, spreading plant with good heat tolerance.

The new cultivar is propagated from cuttings resulting from the cross in September 2000 of the proprietary New Guinea *Impatiens* selection identified as 'G207-1' as female parent and the proprietary New Guinea *Impatiens* selection identified as 'G318-1' as male parent. 'G207-1' is not commercially available and has not been patented. 'G318-1' is not commercially available and has not been patented.

As a result of this cross the present cultivar was selected as a single plant in September 2001 in Enkhuizen, Netherlands and has been repeated asexually reproduced by cuttings in Enkhuizen, Netherlands, in Gilroy, Calif., and in Angers, France over a period of several years. The distinctive characteristics of this new *Impatiens* are stable and reproduced true to type in successive generations of asexual reproduction. It takes 6 to 8 weeks to produce a finished plant, starting from a rooted plug and planted in a 12 cm pot, depending on the temperature.

SUMMARY OF THE INVENTION

The following traits have been repeatedly observed and are determined to be the unique characteristics of 'Ingmulros.' These characteristics in combination distinguish 'Ingmulros' as a new and distinct New Guinea *Impatiens* cultivar:

1. Small, light red flowers with a dark spot in the center
2. Very early flowering with very floriferious habit
3. Small foliage
4. Compact, spreading habit and good heat tolerance Plants of the new New Guinea *Impatiens* differ primarily from the plants of the female parent selection in the following characteristics:

Plants of the New Guinea *Impatiens* have small foliage and a compact, spreading plant habit, whereas the plants of the female parent selection have larger foliage and an upright plant habit.

Plants of the new New Guinea *Impatiens* differ primarily from the plants of the male parent selection in the following characteristics:

Plants of the New Guinea *Impatiens* have light red flowers with dark spot in the center, whereas the plants of the male parent selection have light salmon with dark salmon spot in the center flowers.

Plants of the new New Guinea *Impatiens* can be compared to plants of 'Kinic,' U.S. Pat. No. 11,412. in side-by-side comparisons conducted in Enkhuizen, Netherlands, plants of the new New Guinea *Impatiens* differed from plants of the cultivar 'Kinic' in the following characteristics:

1. Plants of the new New Guinea *Impatiens* have small light red flowers with a dark spot in the center, whereas the plants of the cultivar 'Kinic' have small deep pink flowers with a rose spot in the center.
2. Plants of the new New Guinea *Impatiens* have green leaves, whereas 'Kinic' has dark green leaves.
3. Plant of the new New Guinea *Impatiens* have a good branching, spreading plant habit, whereas plants of 'Kinic' have a branching, upright plant habit.

DESCRIPTION OF THE DRAWING

This new New Guinea *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new New Guinea *Impatiens*. The data which defines these characteristics were collected from asexual reproductions carried out in Enkhuizen, Netherlands. The plant history was taken on 20 week old plants, blossomed under natural light in the field.

Color readings were taken in the laboratory under ambient light. Color references are primarily to The R.H.S. Color Chart of The Royal Horticultural Society of London.

The plant:
- *Classification — Botanical.*—*Impatiens hawkeri.*

Parentage:
- *Female parent.*—Proprietary *Impatiens hawkeri* selection identified as code number 'G207-1,' not patented.
- *Male parent.*—Proprietary *Impatiens hawkeri* selection identified as code number 'G318-1,' not patented.

Propagation:
- *Type cutting.*—Terminal cuttings.
- *Time to initiate roots.*—Approximately 7–14 days.
- *Time to produce a rooted cutting.*—Approximately 21 days.
- *Root description.*—Fine, fibrous, and white in color.

Plant description:
- *General appearance.*—Outwardly spreading, low rounded and uniform mounded plant growth.

Habit:
- *Growth and branching habit.*—Compact and spreading, freely branching habit, freely flowering.

Crop time:
- *Plant height.*—20 cm.
- *Plant spread.*—37 cm.

Lateral branch description:
- *Length.*—13–15 cm.
- *Diameter.*—2–5 mm.
- *Texture.*—Smooth, glabrous.
- *Internode length.*—3.5–5.5 cm.
- *Color.*—RHS 183A.

Foliage description:
- *Arrangement.*—Primarily in whorls.
- *Length, mature leaves.*—6.5 cm.
- *Width, mature leaves.*—1.7–1.9 cm.
- *Shape.*—Lanceolate.
- *Apex.*—Acuminate.
- *Base.*—Attenuate.
- *Margin.*—Serrulate with fine cilation.
- *Texture.*—Smooth, glabrous, leathery.
- *Venation pattern.*—Pinnate.
- *Color young foliage, upper surface.*—RHS 139A.
- *Color young foliage, lower surface.*—RHS 138B.
- *Fully expanded foliage, upper surface.*—RHS N189A.
- *Fully expanded foliage, lower surface.*—RHS 191A.
- *Venation, upper surface.*—RHS 59B.
- *Venation, lower surface.*—RHS 59B.
- *Petiole length.*—About 0.5 cm.
- *Petiole diameter.*—About 1–2 mm.
- *Texture.*—Smooth, glabrous.
- *Color.*—RHS 184A.

Flower description:
- *Flower type and flowering habit.*—Single.
- *Number of flowers per leaf axil.*—1.
- *Number of flowers and flower buds per lateral branch.*—7–8.
- *Flower position.*—Above and beyond the foliage and typically facing upwards and outward.
- *Flower shape.*—Rounded, mostly flat.
- *Flowers lasting.*—About 10 days on the plant depending on environmental conditions.
- *Petals.*—Self cleaning.
- *Gynoecium.*—Persistent.
- *Flowers.*—Not fragrant.
- *Flowering.*—Indeterminate and continuous.
- *Flowering season.*—Year round under greenhouse conditions. In the garden, flowering from spring until fall.
- *Flower length.*—About 3.5 cm.
- *Flower width.*—About 3.9 cm.
- *Flower depth.*—About 0.6 cm.

Flower buds:
- *Bud length.*—About 1.1 cm.
- *Bud diameter.*—About 0.5 cm.
- *Bud shape.*—Ellipsoidal.
- *Texture.*—Smooth.
- *Color, just before opening.*—RHS 60A.

Petals:
- *Quantity.*—Single, five per flower, imbricate.
- *Length of banner petal.*—About 1.5 cm.
- *Width of banner petal.*—About 2.3 cm.
- *Length lateral and basal peals.*—About 2.4 cm.
- *Width lateral and basal petals.*—About 2.4 cm.
- *Lateral and base petal shape.*—Cordate.
- *Banner petal shape.*—Roughly cordate.
- *Petal apex.*—Emarginate.
- *Petal base.*—Attenuate.
- *Petal margin.*—Entire.
- *Petal texture.*—Smooth, velvety.
- *Petal color.*—Upper surface: When opening and fully opened: RHS 50B. Spot in center of flower: RHS 53A. Lower surface: When opening and fully opened: RHS 52D.

Spur:
- *Length.*—About 3.3 cm.
- *Texture.*—Smooth.
- *Aspect.*—Curved.
- *Color.*—RHS 46A.

Peduncles:
- *Length.*—About 3.1 cm.
- *Strength.*—Strong, flexible.
- *Diameter.*—1.5 cm.
- *Aspect.*—About 45° from the stem.
- *Color.*—RHS 46A.

Reproductive organs:
- *Androecium.*—Stamen number: Five fused at anthers, filaments free, hooded.
- *Anther shape.*—Obovate.
- *Anther length.*—About 3 mm.
- *Anther color.*—RHS N66B.
- *Amount of pollen.*—Scarce to moderate.
- *Pollen color.*—RHS 4C.

Gynoecium:
- *Pistil number.*—One.
- *Pistil length.*—About 1.5 mm.

*Stigma shape.*—Columnar, five segmented.

*Stigma color.*—Red purple.

*Style color.*—RHS 142B.

*Ovary arrangement.*—Five celled.

*Ovary color.*—RHS 144B.

Seed development: Seed development has not been observed.

Disease and pest resistance: Resistance to pathogens and pests common to *Impatiens* has not been observed.

What is claimed is:

1. A new and distinct cultivar of New Guinea *Impatiens* plant named 'Ingmulros', as substantially illustrated and described herein.

* * * * *

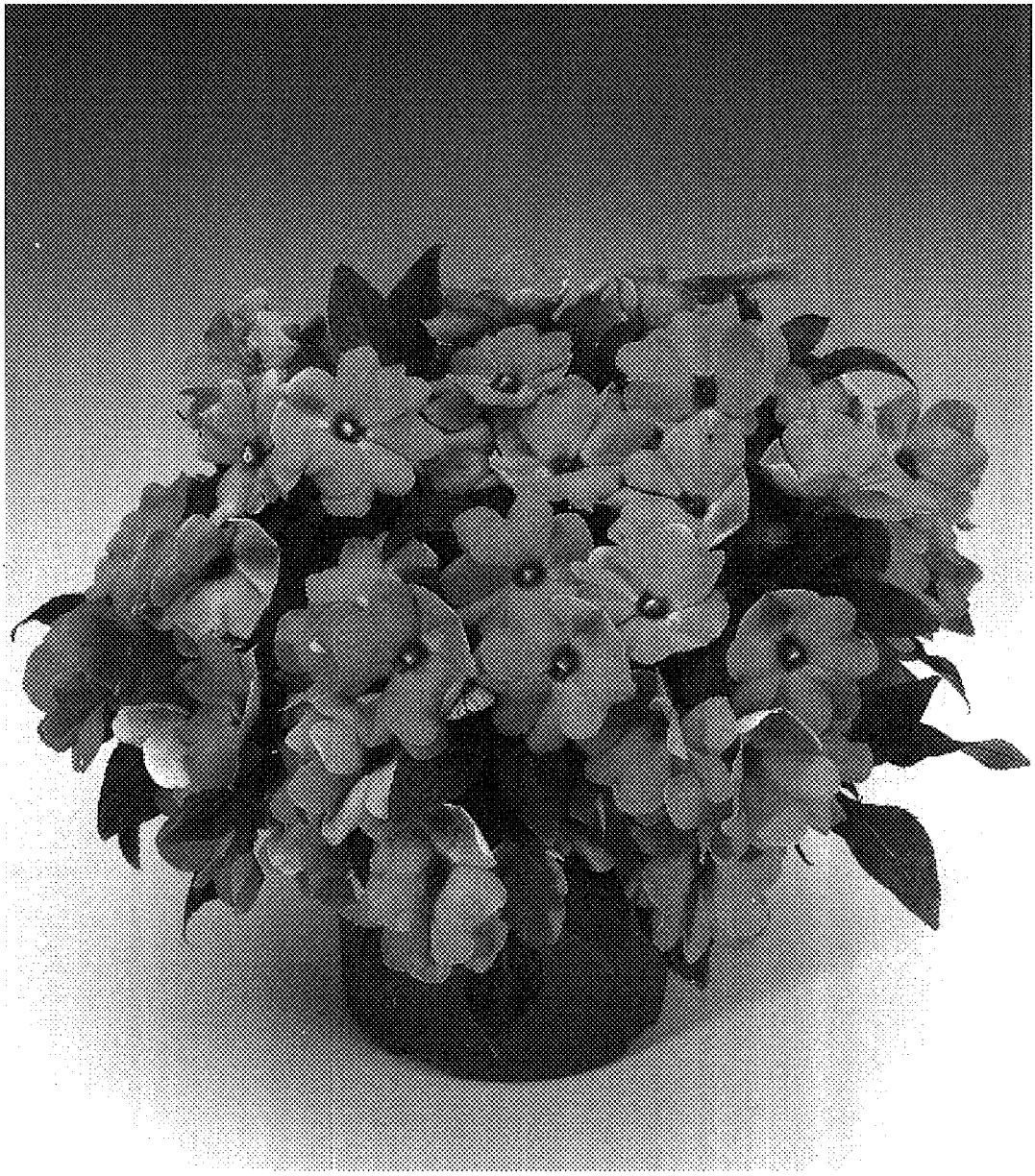

UNITED STATES PATENT AND TRADEMARK OFFICE

CERTIFICATE OF CORRECTION

PATENT NO. : PP 18,242 P2
APPLICATION NO. : 11/436744
DATED : November 20, 2007
INVENTOR(S) : Sanders It is certified that error appears in the above-identified patent and that said Letters Patent is hereby corrected as shown below:

At column 2, line 23, delete “in” and insert therefor --In--.

At column 2, line 33, delete “Plant” and insert therefor --Plants--.

At column 3, line 15, delete “20” and insert therefor --30--.

Signed and Sealed this

Twenty-second Day of July, 2008

JON W. DUDAS
*Director of the United States Patent and Trademark Office*